United States Patent
Ban et al.

(10) Patent No.: US 9,470,630 B2
(45) Date of Patent: Oct. 18, 2016

(54) REFLECTIVE SENSOR FOR DETECTION OF MATERIAL DEGRADATION

(71) Applicant: PD-LD, Inc., Pennington, NJ (US)

(72) Inventors: Vladimir Sinisa Ban, Princeton, NJ (US); Boris Leonidovich Volodin, Pennington, NJ (US); Grzegorz Drozdz, Hamilton, NJ (US); Uri Abrams, Richboro, PA (US)

(73) Assignee: NECSEL INTELLECTUAL PROPERTY, INC., Pennington, NJ (US)

( * ) Notice: Subject to any disclaimer, the term of this patent is extended or adjusted under 35 U.S.C. 154(b) by 0 days.

(21) Appl. No.: 14/865,408

(22) Filed: Sep. 25, 2015

(65) Prior Publication Data

US 2016/0011107 A1    Jan. 14, 2016

Related U.S. Application Data

(63) Continuation of application No. 14/043,149, filed on Oct. 1, 2013, now Pat. No. 9,176,058.

(60) Provisional application No. 61/708,119, filed on Oct. 1, 2012.

(51) Int. Cl.
| | |
|---|---|
| *G01N 21/55* | (2014.01) |
| *G01M 11/08* | (2006.01) |
| *G01M 5/00* | (2006.01) |
| *G01D 5/353* | (2006.01) |
| *G01N 17/04* | (2006.01) |
| *G01D 5/26* | (2006.01) |

(52) U.S. Cl.
CPC .......... *G01N 21/55* (2013.01); *G01D 5/35367* (2013.01); *G01M 5/0008* (2013.01); *G01M 5/0033* (2013.01); *G01M 11/083* (2013.01); *G01M 11/085* (2013.01); *G01N 17/04* (2013.01); *G01D 5/268* (2013.01); *G01N 2201/0886* (2013.01)

(58) Field of Classification Search
None
See application file for complete search history.

(56) References Cited

U.S. PATENT DOCUMENTS

| | | |
|---|---|---|
| 5,367,583 A | 11/1994 | Sirkis |
| 2006/0077379 A1 | 4/2006 | Frot et al. |

(Continued)

OTHER PUBLICATIONS

Wan, Kai Tai, et al., "Durability Tests of a Fiber Optic Corrosion Sensor," Mar. 16, 2012, Sensors 2012, 12, pp. 3656-3668.*

(Continued)

*Primary Examiner* — Gordon J Stock, Jr.
(74) *Attorney, Agent, or Firm* — Condo Roccia Koptiw LLP

(57) ABSTRACT

A sensor for detecting material degradation may include an optical fiber and a housing through which the optical fiber extends. An end cap may be affixed to an end of the housing. Light provided through the optical fiber may be reflected off of the end cap back through the optical fiber. The end cap may be made of a material of interest, and may be situated in an environment wherein the material of interest is present. A light source may provide input light through the optical fiber. A portion of the input light may be reflected off of the end cap. A light receptor may receive the reflected light via the optical fiber. A processing unit may be adapted to compare a measured intensity of the reflected light to a threshold, and to initiate an alarm condition if the measured intensity is below the threshold.

18 Claims, 5 Drawing Sheets

(56) References Cited

U.S. PATENT DOCUMENTS

2008/0141780 A1 6/2008 Wavering et al.
2009/0135427 A1 5/2009 Huang et al.

OTHER PUBLICATIONS

Martins-Filho, Joaquim F., et al., "Multipoint fiber-optic-based corrosion sensor," 2008, Proc. of SPIE vol. 7004, 70043p. 1-4.*
Martins-Filho, Joaquim F., et al., "Fiber-optic-based Corrosion Sensor using OTDR," 2007, IEEE Sensors 2007 Conference, pp. 1172-1174.*
Michael W. Woodruff and J.S. Sirkis, "Corrosion sensing of aluminum using optical fiber," University of Maryland, Department of Mechanical Engineering College Park, Maryland 20742 (1994) SPIE vol. 2191/511.

* cited by examiner

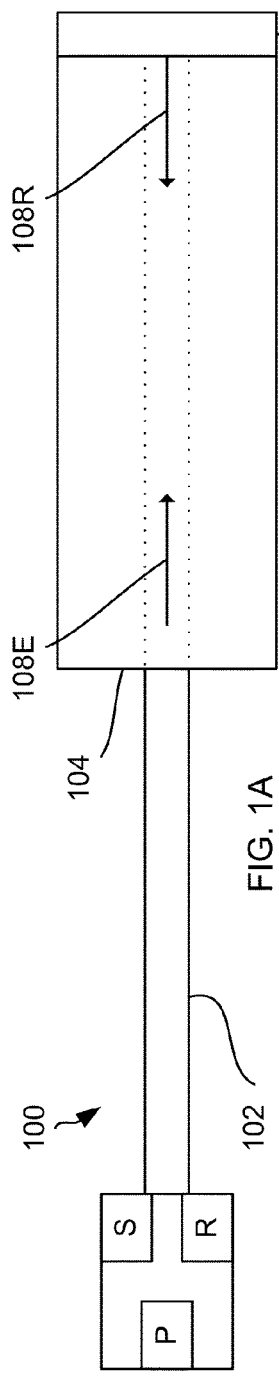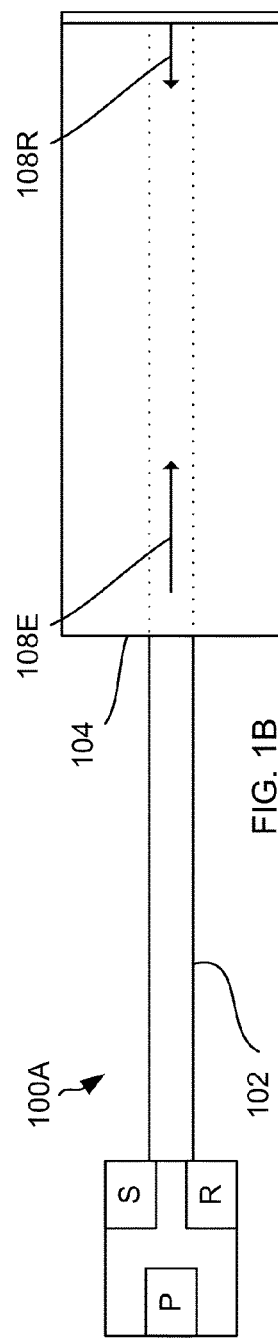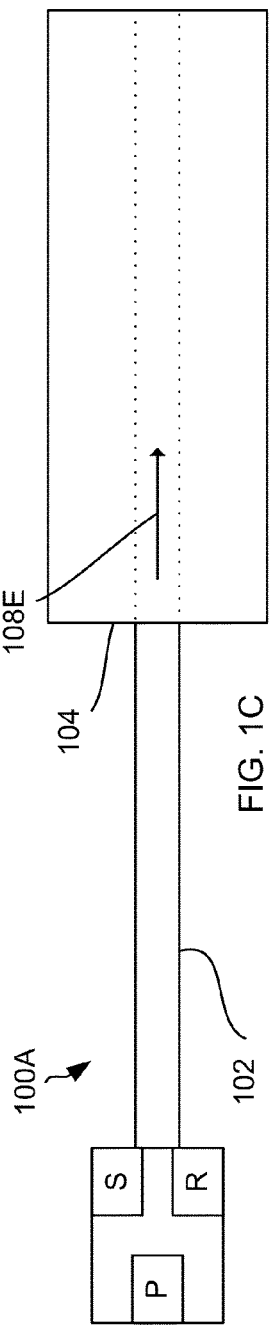

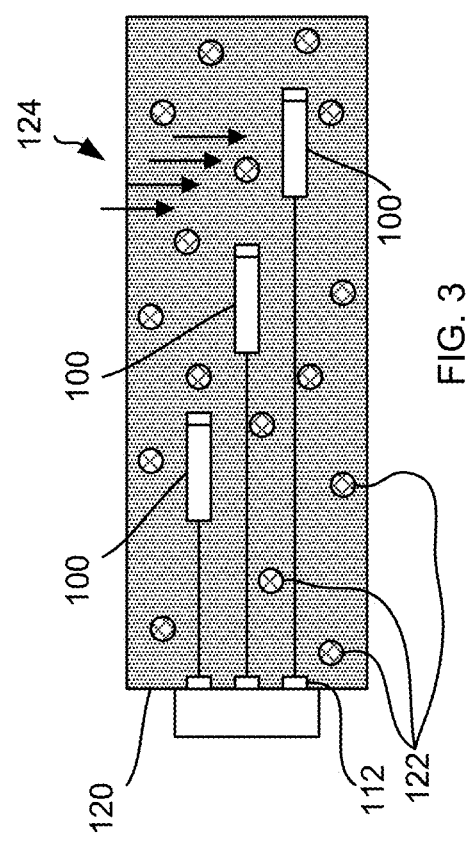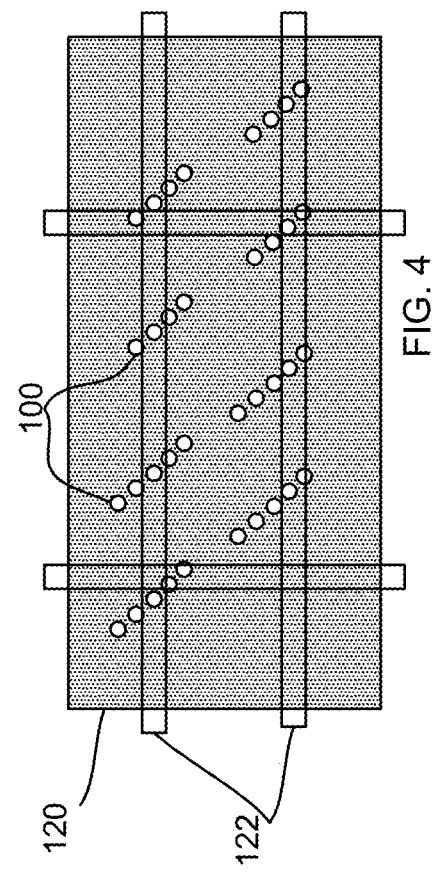

REFLECTIVE SENSOR FOR DETECTION OF MATERIAL DEGRADATION

CROSS-REFERENCE TO RELATED APPLICATIONS

This application claims priority from U.S. patent application Ser. No. 14/043,149, filed Oct. 1, 2013, which claims benefit under 35 U.S.C. §119 of provisional U.S. patent application No. 61/708,119, filed Oct. 1, 2012, the disclosures of each of which are incorporated herein by reference.

BACKGROUND

In some applications, it may be desirable to detect the degradation of certain materials. For example, it may be desirable to detect corrosion of rebar in concrete to determine structural integrity, such as in roadways and bridges, for example. Rebar may be defined as a metal rod or bar used for reinforcement in concrete or asphalt pourings.

Near-infrared (NIR) analysis detects and measures the concentration of chloride ions or other corrosion-causing substances in concrete, but it does not report whether the corrosion of rebar actually took place and to what extent. The presence of chloride, or other substances, such as sulphates or carbonates, for example, may cause corrosion, but other factors also play a role, e.g., moisture, pH, the nature of the concrete and rebar, traffic-caused stress, etc.

It may be desirable, therefore, if there were available a simple, low-cost sensor that is capable of detecting and reporting the occurrence and extent of material degradation, such as the corrosion of rebar in bridge decks, for example.

SUMMARY

As disclosed herein, an example sensor for detecting material degradation may include an optical fiber and a housing through which the optical fiber extends. An end cap may be affixed to an end of the housing. Light provided through the optical fiber may be reflected off of the end cap back through the optical fiber. The end cap may be made of a material of interest, and may be situated in an environment wherein the material of interest is present.

A light source may provide input light through the optical fiber. A portion of the input light may be reflected off of the end cap. A light receptor may receive the reflected light via the optical fiber. A processing unit may be adapted to compare a measured intensity of the reflected light to a threshold, and to initiate an alarm condition if the measured intensity is below the threshold.

An example method for determining material degradation may include situating an end of an optical fiber in proximity to a material. The end of the optical fiber may be abutted against the material, for example. Input light may be provided through the optical fiber such that at least a portion of the input light is reflected off of the material as reflected light. An intensity of the reflected light may be measured.

From the measured intensity of the reflected light, it may be determined whether the material has degraded by more than an acceptable amount. The measured intensity of the reflected light may be compared to a threshold. The threshold may be based on a benchmark intensity of light reflected off of the material before the material begins to degrade. The measured intensity of the reflected light may be compared to the intensity of the input light.

Another example sensor may include an optical fiber having an end that is situated in proximity to a material. The material may be an end cap situated at the end of the optical fiber. The material may be a coating applied directly to the distal end of the fiber. A light source may provide input light through the optical fiber such that at least a portion of the input light is reflected off of the material as reflected light. A light receptor may receive the reflected light via the optical fiber. A processing unit may be adapted to determine from a measured intensity of the reflected light whether the material has degraded.

The processing unit may be adapted to measure the intensity of the reflected light, and to compare the measured intensity of the reflected light to a threshold. The processing unit may be adapted to initiate an alarm condition if it is determined that the measured intensity is below the threshold, or if it is otherwise determined that the material has degraded by more than a predefined amount.

An optical time-domain reflectometer (OTDR) may be employed as the light source and light receptor. The OTDR may also be used to locate faults, such as breaks, for example, in an optical fiber. Use of an OTDR may be particularly suitable where a network of fiber-optic sensors is deployed.

BRIEF DESCRIPTION OF THE DRAWINGS

FIGS. 1A-1C depict an example fiber-optic sensor for detecting material degradation.

FIG. 3 depicts example fiber-optic sensors imbedded in a concrete deck.

FIG. 4 illustrates an example placement of sensors in a test concrete deck.

DETAILED DESCRIPTION

Figure 2:
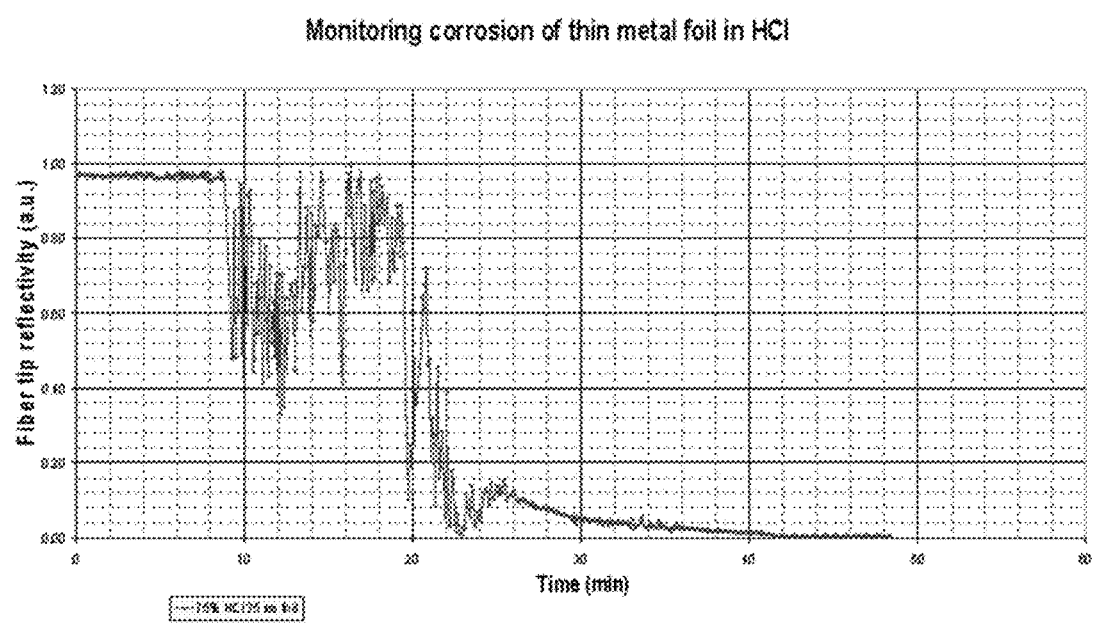
FIG. 2 provides the results of an accelerated material degradation test.

FIGS. 1A-1C depict an example fiber-optic sensor 100. Such a sensor 100 may be particularly suitable for detecting corrosion of rebar in a concrete structure. It should be understood, however, that such a sensor may also be useful for detecting degradation of other materials, such as paint, plastic, TEFLON, brake padding, or a noble metal, for example. As used herein, the term "degradation" may be used liberally to refer to any change in the condition of a material, such as by degradation, deterioration, dissolution, corrosion, erosion, abrasion, oxidation, delamination, or other wear, for example.

As shown, the sensor 100 may include an optical fiber 102, a housing 104, and an end cap 106. Optical fibers are well-known, and need not be described in detail herein. Suffice it to say that the optical fiber 102 may be made of any desirable optical material such that light may pass through the optical fiber 102 in both directions from one end to the other. The optical fiber 102 may extend through the housing 104. The optical fiber 102 may be one of a plurality of optical fibers that extends through the housing 104. Such a structure—a plurality of optical fibers contained by a housing—may be referred to as an optical cable.

The housing 104 may be made of steel, for example. It should be understood, however, that the housing 104 may be made of any suitable material, such as iron, ceramic, glass, plastic, polymer, or any of a number of various metals, for example. The housing 104 may be formed to have the shape of a hollow cylinder. It should be understood, however, that the housing 104 may be formed to have any desirable shape, such as a flat plate or a box, for example. A box-shaped housing may be particularly desirable where an arrangement of optical fibers is provided within a single housing. Such an arrangement may be a linear or two-dimensional array of optical fibers, for example. An example cylindrical housing 104 may have a length of about 12 mm and a radius of about 2.5 mm. It should be understood, however, that the housing 104 may have any desirable dimensions.

The end cap 106 may be made of any material that the sensor 100 is designed to monitor. For example, in an application where the sensor 100 is designed to monitor rebar in a concrete installation, the end cap 106 may be made of the same material as the rebar, e.g., steel.

The end cap 106 may be affixed to an end of the housing 104. The end cap 106 may be affixed to the end of the housing 104 by any desirable means, such as by epoxying, gluing, welding, or brazing, for example. The optical fiber 102 may abut the end cap 106. It should be understood that the end cap 106 is optional, and that the distal end of the optical fiber 102 may be situated in proximity to the material that the sensor 100 is designed to monitor. For example, if the material to be monitored is paint, the distal end of the optical fiber 102 may be abutted against the paint itself. Instead of an end cap, the distal end of the optical fiber 104 may be coated directly with a layer of the material of interest. For example, the distal end of the optical fiber 104 may be coated with a layer of paint, or a metal may be sputter-coated onto the end of the fiber 104.

The optical fiber 104 may carry light 108E that is emitted from a light source S, through the optical fiber 102, to the end cap 106. The emitted light 108E may be reflected off of the end cap 106 as reflected light 108R, and travel back through the optical fiber 102, to a light receptor R. A processing unit, P, may be provided to measure an intensity of the reflected light. The processing unit P may be further adapted to compare the measured intensity of the reflected light to a threshold. The processing unit P may be further adapted to initiate an alarm condition if the measured intensity is below the threshold.

Based on the intensity of the reflected light 108R, the sensor 100 can determine the extent to which the end cap 106 has degraded. The sensor 100 may determine whether the material from which the end cap 106 is made has degraded by more than a certain amount by comparing the intensity of the reflected light 108R to a threshold. Thus, over time, when an insufficient amount of the emitted light is being reflected back, the sensor 100 can conclude that the material has degraded too much. The threshold may be based on the intensity of the emitted light 108E. Thus, the sensor could compare the intensity of the reflected light 108R to the intensity of the emitted light 108E. The threshold may be based on a benchmark intensity of the reflected light 108R, i.e., an intensity of the reflected light 108R as measured before the sensor 100 is placed into service. Thus, the sensor could compare the intensity of the reflected light 108R to its initial intensity before the material began to degrade. The threshold may be preset based on the nature of the material being monitored. The threshold could be effectively zero. That is, the sensor could monitor the reflected light until the material has degraded sufficiently that no appreciable amount of light is reflected back.

FIG. 1A depicts the sensor 100 during the early stages of its operation with a newly installed end cap 106. In this example, the reflected light 108R has a first (benchmark) intensity. FIG. 1B depicts the sensor 100 at some point during its life with a degraded end cap 106A. In this example, the reflected light 108R has a second intensity that is less than its benchmark intensity due to degradation of the end cap 106. FIG. 1C depicts the sensor 100 at a point in its life when the end cap has completed degraded away. In this example, there might be no appreciable amount of reflected light.

In a bridge application, where the sensor 100 is being employed to detect the degradation of rebar in concrete, the end cap 106 may be made of steel. Light reflected off the end cap 106 may have a benchmark intensity before the end cap 106 begins to degrade. When the end cap 106 begins to degrade, the intensity of the reflected light 108R will be reduced relative to its benchmark intensity. Eventually, the end cap will degrade to a point where further degradation is no longer tolerable. At that point, the reflected light 108R will have a threshold intensity. When the sensor detects that the reflected light has an intensity that is less than the threshold intensity, the sensor can conclude that the end cap has degraded by an unacceptable amount. Because the end cap is made of the same material as the material being monitored (e.g., rebar in a concrete installation), it may be assumed that the actual rebar has also degraded to below a certain, acceptable level. The thickness of cap may be chosen such that when the cap has corroded away completely, it may be assumed that the corresponding material in the installation has corroded more than an acceptable level.

Several sensors were tested by the accelerated corrosion in HCl solutions. FIG. 2 shows the results of an accelerated corrosion test in HCl. Prior to corrosion, the reflected light signal was very strong. After the onset of the corrosion, the reflected light signal was very weak.

FIG. 2 provides the results of the accelerated corrosion test as a function of reflectivity over time. In the test, the distal end of the optical fiber was abutted against a 25-micron thick sheet of steel foil. The foil-tipped optical fiber was immersed in HCl. As shown in the graph, the reflectivity remained relatively constant for about nine minutes after the foil-tipped optical fiber was immersed. After that, the onset of degradation could be detected as evidenced by the varying reflectivity. It can be observed from the vacillations in the reflectivity between nine and 20 minutes that not only did the foil degrade, but also separated in distance from the tip of the optical fiber. Thus, a sensor as described herein can also be used to detect separation in distance between the optical fiber and the material of interest. After about 22 minutes, the reflectivity fell off significantly relative to benchmark. Eventually, when the foil was completely dissolved, the reflectively remained constant at a very low level relative to benchmark.

Such fiber-optic sensors may be useful for monitoring corrosion in bridge decks and other concrete structures. Such sensors may be embedded into concrete decks, which may be under construction. Since the sensors unambiguously detect the onset of corrosion, they may serve as a calibration for other corrosion detection methods.

FIG. 3 depicts a plurality of sensors 100 embedded in a concrete deck 120. Placement of sensors 100 at different depths enables monitoring of the rate of penetration of chloride ions (shown as arrows in FIG. 3) into the deck 120. Sensors 100 may be placed at different depths to monitor the penetration of chloride ions. The fibers may be connectorized, and the connectors 112 may be placed in a terminal box 110 at the edge of the deck, where they can be accessed for occasional measurements of the reflected signal, i.e., to detect the onset of the corrosion.

As shown in FIG. 3, any number of sensors 100 can be embedded at various locations in an environment of interest, such as in an environment of rebar-enforced concrete as might be used to form a bridge deck. The concrete 120 may have any number of reinforcing rods (rebar) 122 running throughout it. The rods 122 may be made of steel. The end caps on the sensors 100 may be made of the same steel as the rods 122.

In such an environment, the onset of the corrosion of the steel rods may indicate that sufficient chlorine has penetrated the structure to make it unsafe. Thus, the penetration of chlorine may be detected by detecting degradation of the end caps. End caps can be of different thicknesses to measure the rate of corrosion. Sensors can be placed at various depths from the surface of the bridge deck to follow accurately the penetration of the chloride ions at various locations of the bridge deck.

It is estimated that a steel cap having a thickness of about one millimeter may resist degradation in concrete for several years. It should be understood however, that the sensors described herein may be used to detect degradation or wear of any material, such as glass, metal, or any other material of interest. In general, the end cap may have a thickness ranging from about one mil to a few millimeters, or more, depending on the material being monitored, and the expected rate of degradation in the particular application, which may be several hours, or several years. For example, rebar may show the onset of corrosion in only a few months, for example, should the surrounding chloride concentration reaches the corrosion threshold values of about 0.04% of chloride by weight.

In test decks, various methods for the acceleration of the corrosion may be applied. FIG. 4 depicts a possible placement of sensors 100 in a test concrete deck 120 at various positions relative to a plurality of rebars 122. Readings obtained from fiber-optic sensors 100 may be used to cross-calibrate other corrosion detection methods (e.g., ground radar, acoustic methods, etc). The combination of various X and Y locations (i.e., position), and of Z placements (i.e., depth), will give a complete picture of the chloride penetration and the corrosion in the deck instrumented in this way.

Figure 5:
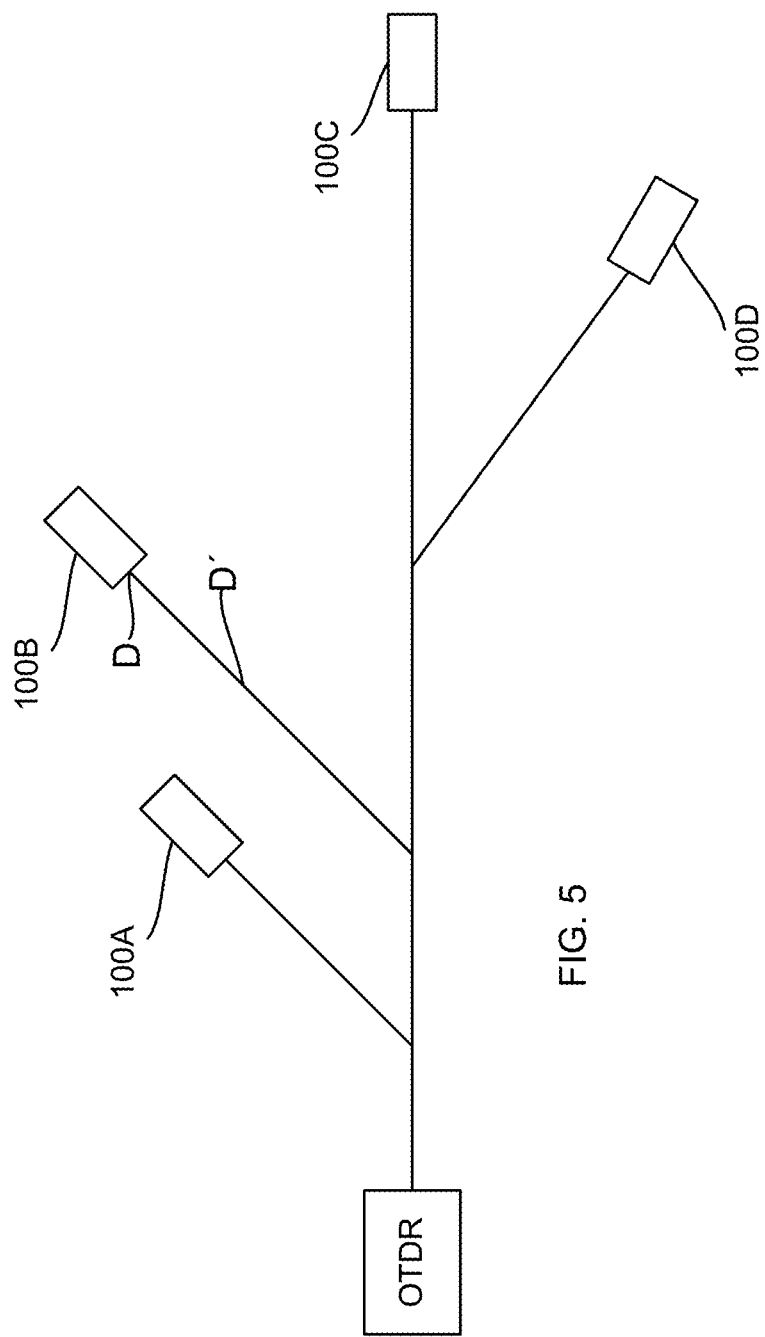
FIG. 5 depicts an example sensor system including an optical time-domain reflectometer (OTDR).

FIG. 5 depicts an example sensor system including an optical time-domain reflectometer (OTDR). An OTDR is an optoelectronic instrument used to characterize an optical fiber. OTDRs are well-known, and need not be described herein in detail. In essence, an OTDR injects a series of optical pulses into the optical fiber. It also extracts, from the same end of the fiber, light that is scattered or reflected back from points along the fiber. The strength of the return pulses may be measured and integrated as a function of time. Thus, faults in the fiber, such as breaks, for example, may be detected and the location of such faults determined.

As shown in FIG. 5, under normal operating conditions, pulses emitted from the OTDR will reflect back from the sensors 100A-D through the fiber network to the OTDR. The processing unit can determine from the strength of the reflected pulses whether the material of interested has degraded below an acceptable level. The OTDR can determine the distance from which the pulses were reflected. For example, as shown, sensor 100B may be located a distance D from the OTDR. Under normal operating conditions, a significant pulse will be reflected by the sensor 100B. The OTDR will determine that a significant pulse was reflected from the sensor 100B, and conclude, therefore, that the material has not yet degraded below threshold.

If there is no significant reflection from a distance D, the OTDR can determine that the sensor 100B has detected a material degradation. A map as to the locations of the one or more sensors making up the network can be provided to the processing unit, so that the processing unit knows how far away the various sensors are placed. If an insignificant reflection, or none at all, comes from the location of any of the sensors, the OTDR can identify the locations where the material has degraded.

An OTDR may also be used to detect faults, such as breaks, in the optical fibers. Suppose, for example, that a break, crack, or other anomaly occurs in the optical fiber leading to sensor 100B, at a distance D' from the OTDR. The anomaly will cause an unexpected reflection. When the OTDR detects a reflection from a location in the network other than where a sensor is located (e.g., the map would indicate no sensor at D'), the OTDR can determine that there must be a fault in the optical fiber at that location. Thus, the OTDR may be used to interrogate the optical fiber network for faults.

Figure 6:
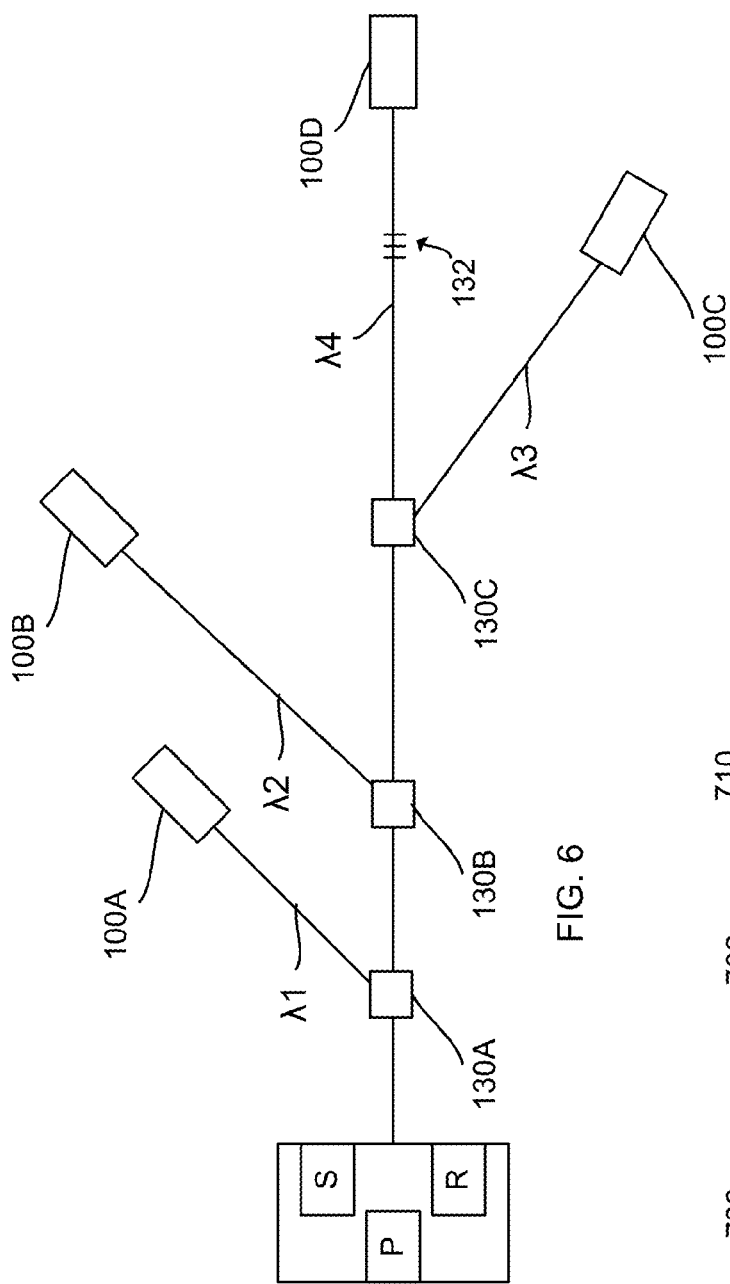
FIG. 6 depicts an example sensor system based on wavelength detection.

Sensors such as described herein may be adapted to detect the wavelength of the reflected light. For example, signals of different wavelengths may be routed to different sensors. FIG. 6 depicts a sensor system based on wavelength detection. As shown, one or more wavelength selective elements 130A-C may be situated at respective fiber junctions. Light emitted from the light source may contain light having any number of wavelengths. For example, the system may employ LEDs of various wavelengths to provide input light.

A first element 130A may cause light having a wavelength $\lambda 1$ to be directed toward sensor 100A, while the remainder of the light passes through. Thus, element 130A may be transparent to the remainder of the light. Likewise, element 130B may cause light having a wavelength $\lambda 2$ to be directed toward sensor 100B, and element 130C may cause light having a wavelength $\lambda 3$ to be directed toward sensor 100C. Elements 130A-C may all be transparent to light having wavelength $\lambda 4$, which would be directed toward sensor 100D. The processing unit may determine from the reflectivity of light having a certain wavelength which of the sensors has detected a material degradation.

Wavelength selective elements are well known. In particular, volume Bragg grating elements may be used as wavelength selective elements in a sensor system as described herein. The use of volume Bragg grating elements as wavelength selective elements is described in U.S. Pat. No. 7,031,573, the disclosure of which is incorporated herein by reference.

It should be understood that fiber Bragg gratings 132 may be recorded in one or more of the optical fibers. In such an example, the fibers in the network that have the Bragg gratings recorded therein may be used as strain gauges. For example, it is known that, when the fiber stretches, the peak wavelength of the fiber Bragg grating shifts. Such a shift may indicate that the fiber has been stretched, due to some condition, such as strain on the environment in which the sensor is deployed (bridge strain, for example). Thus, such a sensor may be used as a strain gauge as well as a sensor for material degradation in combination.

In another example, a sensor system may be adapted to monitor for the presence of a chemical. For example, the distal end of the optical fiber may be coated with a material that would react with the chemical of interest. The spectrum of the reflected light may be a function of the color of the material. The fiber may be placed in proximity to the area to be monitored for the chemical of interest. If the chemical of interest is present, then a chemical reaction with the material would cause the color of the material, and therefore the spectrum of the reflected light, to change. Thus, the presence of a chemical of interest may be determined from the spectrum of the reflected light. In such a sensor, the processing unit may be adapted to perform spectrum analysis on the reflected light to detect changes in the spectrum thereof.

In another example, a sensor system may be adapted to detect changes in pH. For example, the distal end of the optical fiber may be coated with a pH-sensitive material. The spectrum of the reflected light may be a function of the color of the pH-sensitive material. The fiber may be placed in proximity to the material of interest, which may cause the pH-sensitive material to assume a color based on the pH of the material of interest. Thus, the pH of the material of interest may be determined from the spectrum of the reflected light. In such a sensor, the processing unit may be adapted to perform spectrum analysis on the reflected light to detect changes in the spectrum thereof.

In another example, a sensor system may be adapted to determine the distance between the distal tip of the fiber and the material of interest. Such a system may be adapted to detect changes in the distance between the distal tip of the fiber and the material of interest. The spectrum of the reflected light may be a function of the distance between the distal tip of optical fiber and the material of interest. As the distance between the distal tip of the optical fiber and the material of interest changes, so does the spectrum of the reflected light. Thus, such a sensor may be used to detect static changes in the distance between the fiber and the material of interest, as well as dynamic changes, such as caused by acoustic vibrations, for example. In such a sensor, the processing unit may be adapted to perform spectrum analysis on the reflected light to detect changes in the spectrum thereof.

Figure 7:
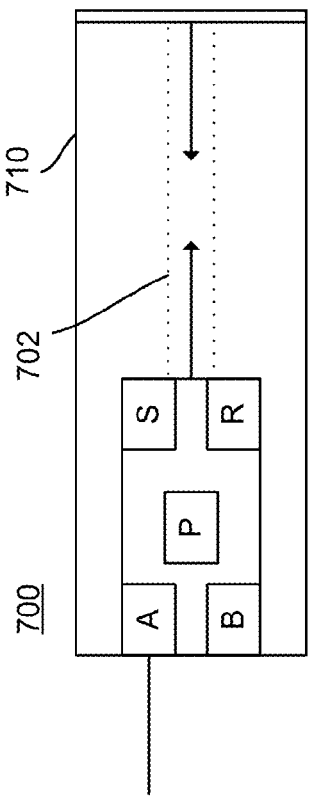
FIG. 7 depicts an example sensor capsule with wireless communication.

FIG. 7 depicts an example sensor capsule 700 with wireless communication. The capsule 700 is a self-contained unit that includes a light source S, a light receptor R, a processing unit P, a power source, B, which may be a battery, and an antenna A, all of which may be contained in a housing 710. As described herein, light emitted from the light source S through an optical fiber 702 may be reflected off of material M situated at an end of the capsule 700 back through the optical fiber 702 to the receptor R. The material may be in the form of an end cap, or it may be coated onto the end of the capsule, or the capsule may merely be situated in proximity to the material. The antenna may be used to communicate signals wirelessly from the capsule 700 to a monitoring station (not shown). For example, the sensor may be adapted to text the integrity of the material periodically (e.g., once every couple of months or so) and transmit a signal indicating whether the material has degraded or not. Such signals may include an identity of the sensor capsule. Thus, the monitoring station may be informed of the location of the material degradation. Such an embodiment may eliminate the need for the sensors to be physically connected to a monitoring station.

In another example, sensors as described herein may be used in medical applications. For example, such a sensor may be ingested or implanted in such a way as to monitor biological systems, such as bone, for example, for deterioration or the onset of disease.

The invention claimed is:

1. A sensor system for detecting degradation of a material of interest embedded in a structure, the sensor system comprising:
an optical fiber;
a housing through which the optical fiber extends;
an optical time-domain reflectometer (OTDR) that injects a series of optical pulses into the optical fiber; and
an end cap disposed at an end of the optical fiber such that the pulses injected into the optical fiber are reflected off of the end cap back through the optical fiber, wherein the end cap is made of the material of interest and has a thickness corresponding to a threshold level of degradation of the material of interest in the structure, and
wherein the OTDR extracts from the optical fiber pulses that are reflected off of the end cap, and the OTDR determines, based on a distance from which the pulses were reflected, whether the material of interest has degraded below the threshold.

2. The sensor system of claim 1, wherein the OTDR injects the optical pulses into an end of the optical fiber, and extracts the reflected pulses from the same end of the optical fiber.

3. The sensor system of claim 1, wherein the OTDR determines the distance from which the pulses were reflected.

4. The sensor system of claim 1, wherein a strength of the reflected pulses is measured and integrated as a function of time.

5. The sensor system of claim 4, wherein the OTDR determines, based on the strength of the reflected pulses, whether the material of interest has degraded below the threshold.

6. The sensor system of claim 5, wherein the OTDR determines, based on the strength of the reflected pulses, that the material of interest has not degraded below the threshold.

7. The sensor system of claim 5, wherein the OTDR determines, based on the strength of the reflected pulses, that the material of interest has degraded below the threshold.

8. A sensor network for detecting degradation of a material of interest embedded in a structure, the sensor network comprising:
a plurality of sensors embedded at various locations in the structure; and
an optical time-domain reflectometer (OTDR),
wherein each of the sensors comprises a respective optical fiber, a respective housing through which the optical fiber extends, and a respective end cap disposed at an end of the optical fiber,
wherein each of the end caps is made of the material of interest and has a respective thickness chosen such that when the end cap has degraded by a certain amount, the material of interest has degraded to below a threshold level, and
wherein the OTDR injects a respective series of optical pulses into each of the optical fibers, receives respective reflected pulses reflected off of the respective end caps, and determines, based on respective distances from which the reflected pulses were reflected, a location within the structure at which the material of interest has degraded to below the threshold level.

9. The sensor network of claim 8, wherein the OTDR extracts the reflected pulses from the optical fibers.

10. The sensor network of claim 8, wherein the OTDR injects the optical pulses into respective ends of the optical fibers, and extracts the respective reflected pulses from the same ends of the optical fibers.

11. The sensor network of claim 8, wherein the OTDR determines the respective distances from which the pulses were reflected.

12. The sensor network of claim 8, wherein strengths of the reflected pulses are measured and integrated as a function of time.

13. The sensor network of claim 12, wherein the OTDR determines, based on the strengths of reflected pulses received from a determined distance associated with a location in the network, whether the material of interest has degraded below the threshold at that location.

14. The sensor network of claim 12, wherein the OTDR determines, based on the strengths of reflected pulses received from a determined distance associated with a location in the network, that the material of interest has not degraded below the threshold at that location.

15. The sensor network of claim 12, wherein the OTDR determines, based on the strength of a reflected pulse received from a determined distance associated with a location in the network, that the material of interest has degraded below the threshold at that location.

16. The sensor network of claim 8, further comprising a map of respective locations of the plurality of sensors in the network.

17. The sensor network of claim 8, wherein the end caps have different thicknesses.

18. The sensor network of claim 17, wherein a rate of corrosion of the material of interest in the structure is determined based on reflections off of the end caps of different thicknesses.

* * * * *